US00PP15160P3

(12) United States Plant Patent
Tancredi, Jr.

(10) Patent No.: US PP15,160 P2
(45) Date of Patent: Sep. 21, 2004

(54) PHOTINIA PLANT NAMED 'CASSINI'

(50) Latin Name: *Photinia×fraseri*
Varietal Denomination: Cassini

(75) Inventor: Robert J. Tancredi, Jr., Salem, OR (US)

(73) Assignee: CP Delaware, Inc., Wilmington, DE (US)

( * ) Notice: Subject to any disclaimer, the term of this patent is extended or adjusted under 35 U.S.C. 154(b) by 20 days.

(21) Appl. No.: 10/185,046

(22) Filed: Jul. 1, 2002

(65) Prior Publication Data

US 2004/0003442 P1 Jan. 1, 2004

(51) Int. Cl.[7] ..... A01H 5/00
(52) U.S. Cl. ..... Plt./226

(58) Field of Search ..... Plt./226

*Primary Examiner*—Howard J. Locker
(74) *Attorney, Agent, or Firm*—Burns, Doane, Swecker & Mathis, L.L.P.

(57) ABSTRACT

A new and distinct highly ornamental variety of *Photinia×fraseri* plant is provided. An upright outwardly-spreading shrub is described that has a more compact growth habit as the plant ages than commonly is displayed by *Photinia×fraseri.* Attractive variegated foliage is displayed. Initially the foliage is reddish with pink margins that changes to green with pink margins. Finally the leaf margins mature to near white with near white and silver splashes over the green medial upper surfaces of the leaves. The new variety propagates well by the use of stem cuttings and grows well in U.S.D.A. Hardiness Zone Nos. 6(b) to 10. The plant is well suited for growing as an ornamental specimen or in the form of a distinctive hedge. Also, the unusual color foliage can be used to advantage as a part of flower arrangements.

3 Drawing Sheets

Figure 1:
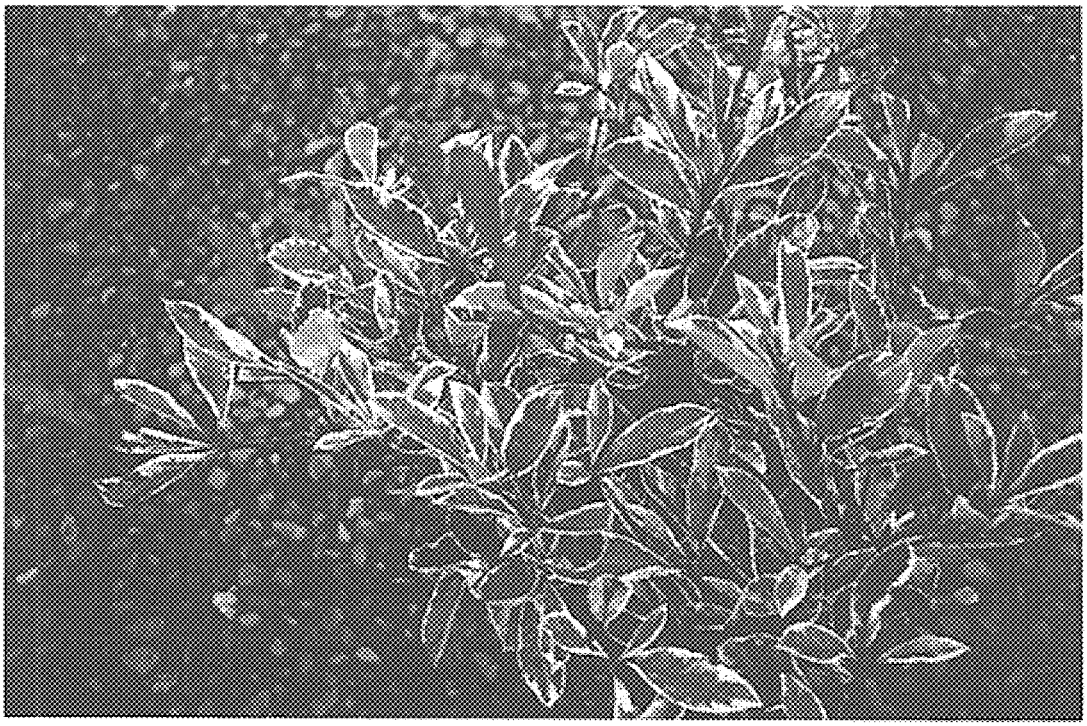

Botanical/commercial classification: *Photinia×fraseri*/ Photinia Plant.
Varietal denomination: cv. 'Cassini'.

SUMMARY OF THE INVENTION

The invention relates to a new and distinct selection of *Photinia×fraseri,* a member of the rose family, Rosaceae.

The new variety of the present invention was discovered during 1991 while present in a block of container-grown *Photinia×fraseri* plants (non-patented in the United States) that had been reproduced through the user of cuttings at Salem, Oreg. and at West Grove, Pa. A single plant of the new variety was discovered and was carefully preserved and studied in view of its distinctive combination of characteristics. The new variety of the present invention is believed to be a spontaneous bud sport mutation of unknown causation. Had the new variety not been discovered and preserved it would have been lost to mankind.

It was found the new *Photinia×fraseri* variety exhibits the following combination of characteristics:

(a) an upright outwardly-spreading broad-leaved evergreen shrub that has a more compact growth habit as the plant ages than commonly is displayed by *Photinia×fraseri,*

(b) forms distinctive variegated foliage that is initially reddish with pink margins, changing to green with pink margins, and with the margins finally maturing to near white with near white and silver splashes over the green medial upper surfaces of the leaves, (c) propagates well by the use of stem cuttings, and (d) is well suited for providing attractive ornamentation in the landscape.

The new variety can be readily distinguished from its *Photinia×fraseri* parent which lacks the distinctive variegated foliage and the more compact growth habit.

When grown as a two year-old juvenile plant in containers, the new variety appears to display substantially the same growth rate as the parental *Photinia×fraseri.* However, as the new plant further ages a more compact growth habit commonly is observed than the parent. Young plants of the new variety have been observed to grow more vigorously in containers under nursery growing conditions with ample fertilization and water than when growing outdoors in the ground. For instance, a five year-old plant of the new variety growing in a five or ten gallon container may produce in a given season up to approximately 36 inches of terminal growth and up to approximately 18 to 24 inches of lateral branches. Alternatively, when grown in the ground, a plant of the same age may produce approximately 12 to 18 inches of terminal growth and approximately 3 to 6 inches of lateral growth.

The new variety well meets the needs of the horticultural industry and can be grown in the landscape as a colorful specimen plant or to form a hedge. The new variety also can serve as a source of unusual colorful cut foliage for use in flower arrangements.

Asexual reproduction of the new variety by the use of stem cuttings at Salem, Oreg. and at West Grove, Pa. has demonstrated that the unique combination of characteristics of the new variety is firmly fixed and is retained through successive generations of asexual propagation.

The new variety of the present invention has been named 'Cassini', and is being marketed under the PINK MARBLE trademark. 'Cassini' has not been observed under all possible environmental conditions to date. Accordingly, it is possible that the phenotype may vary somewhat with variations in the environment, such as temperature, light, day length, cultural conditions, etc.

BRIEF DESCRIPTION OF THE PHOTOGRAPHS

The accompanying photographs show, as true as is reasonably possible to make the same in color illustrations of this character, typical plants of the new variety. The plants were approximately five years of age and were being grown in containers.

FIG. 1 shows primarily the typical distinctive mature foliage of the new variety. Such leaves are shown to display variegated upper leaf surfaces that are green with irregular near white margins and splashes of white and silver. Some immature reddish foliage also is present primarily at the upper left portion of the photograph. The plant was grown at Salem, Oreg.

Figure 2:
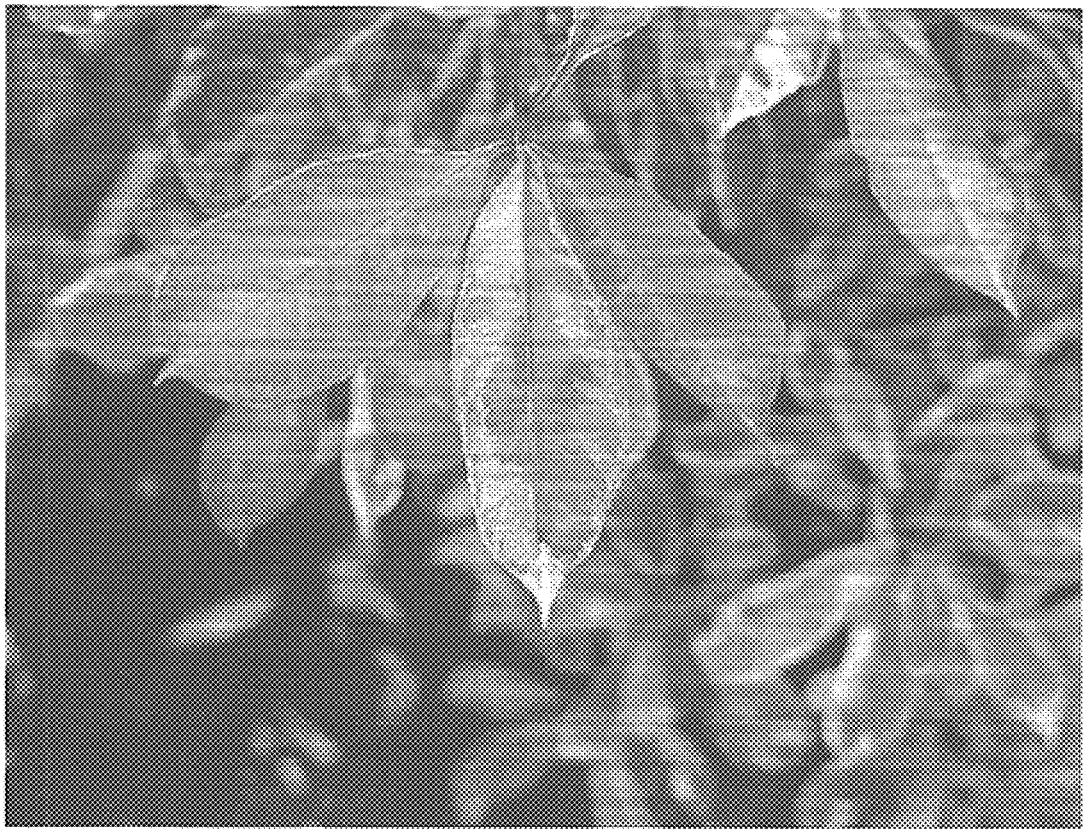

FIG. 2 shows at the forefront the typical colorful immature reddish foliage, as well as the variegated leaves of advancing maturity with pink margins and some overlay white and silver splashes. The plant was grown at West Grove, Pa.

Figure 3:
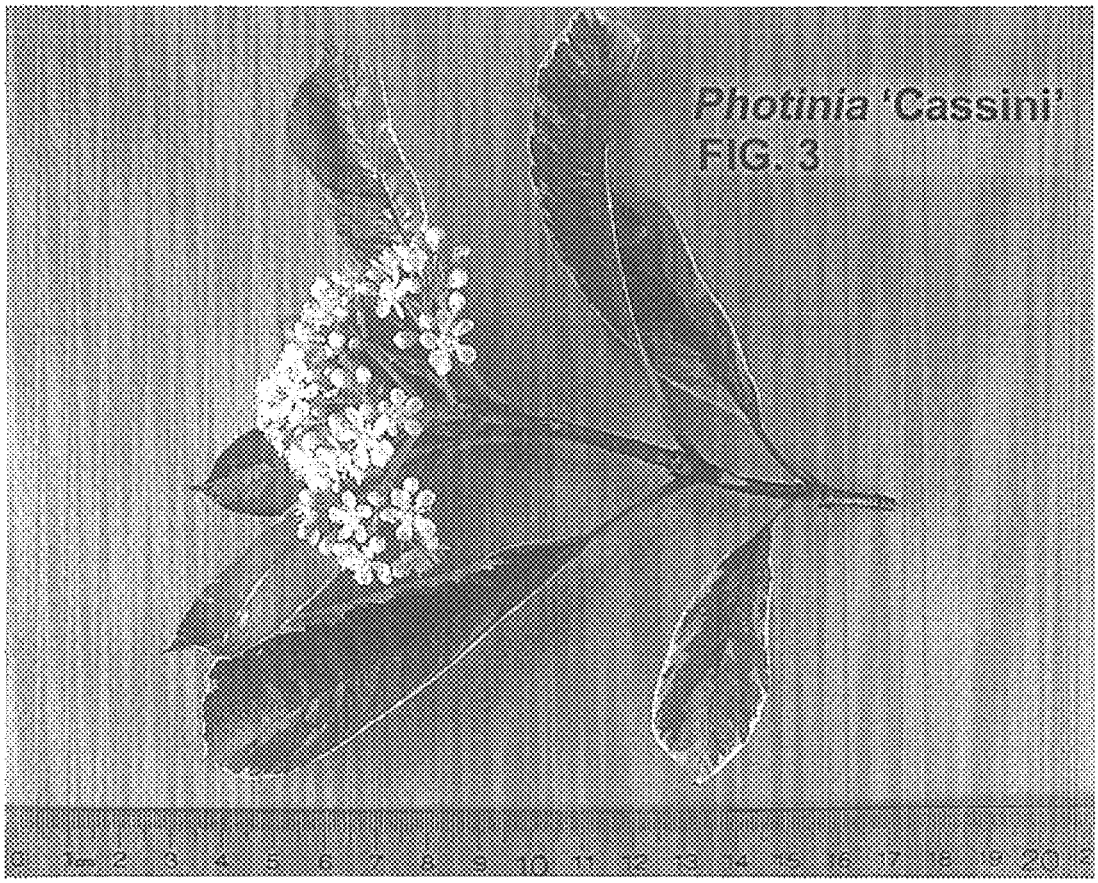

FIG. 3 shows a typical terminal inflorescence with one leaf having been removed for clarity. The photograph was taken on May 2, 2003 at West Grove, Pa. Dimensions in centimeters are included at the bottom.

DETAILED DESCRIPTION

The description is based upon the observation of five year-old plants propagated by the use of stem cuttings that were growing in unheated plastic-covered greenhouses in containers at West Grove, Pa. The chart used in the identification of the colors in The R.H.S. Colour Chart of the Royal Horticultural Society, London. Other color terminology used in the description is to be accorded its ordinary dictionary significance.

Plant:

*Type.*—Perennial, broad-leaved evergreen shrub.

*Growth habit.*—Multistemed, upright and outwardly-spreading and more compact than its *Photinia*× *fraseri* parent.

*Branching habit.*—Freely-branching, and responds well to pruning.

*Height.*—Approximately 6 feet and approximates that of *Photinia glabra.* This compares to approximately 7 to 10 feet for the parent.

*Width.*—Approximately 4 to 5 feet and approximates that of *Photinia glabra.* This compares to approximately 6 to 8 feet for the parent.

Foliage:

*Bearing.*—Simple and alternate.

*Configuration.*—Typically oblanceolate to narrowly obovate to obovate to rarely elliptical to narrowly elliptical and occasionally falcate.

*Apex.*—Typically abruptly acuminate to occasionally acute.

*Base.*—Narrowly cuneate.

*Margins.*—Occasionally undulate, serrulate and at times irregularly so with the serrations tending to be closer together nearing the tip (as illustrated in FIG. 2).

*Texture.*—Glabrous and coriaceous.

*Length.*—Commonly approximately 5 to 14 cm, with mature leaves frequently measuring approximately 10 to 12 cm in length.

*Width.*—Commonly 2.5 to 5.5 cm, with mature leaves frequently measuring approximately 3.5 to 5.0 cm in width.

*Immature foliage upper surface.*—Margins: mixture of Red-Purple Group 58D, Red-Purple Group 63C, and Red-Purple Group 65A. Medial areas: primarily Green Group 139A with small scattered areas of various shades near Greyed-Green Group 189B with some of the same margin coloration being scattered throughout and overlaying in a random array of shapes and sizes.

*Immature foliage lower surface.*—The base coloration is near Greyed-Green Group 194B and is overlaid with Greyed-Purple Group 186B.

*Mature foliage upper surface.*—Margins: well-defined and mostly near Yellow-White Group 158B. Medial areas: near Green Group 139A with randomly scattered areas of various shapes near Greyed-Green Group 189A and 189B.

*Mature foliage lower surface.*—Mostly near Greyed-Green Group 191B with near white margins near Yellow-White Group 158B.

*Petiole.*—Configuration: commonly grooved on the ventral surface. Length: commonly ranges from approximately 0.5 to 2.5 cm in length. Diameter: commonly ranges from approximately 1.6 to 2.5 mm. Color of upper surface: mostly Green Group 139A in the groove, and shading into and near Greyed-Purple Group 184A. Color of lower surface: mostly near Yellow-Green Group 147D, and shading into and near Greyed-Purple Group 184A.

*Stems.*—Young stems on current season's growth are near Red Group 46A in coloration.

Flowers:

*Form.*—Perfect, polypetalous, actinomorphic, and five-petaled.

*Bearing.*—Commonly in a loose corymbose panicle, typically flattened to slightly mounded. Flowers have been observed on plants as young as three years.

*Size.*—Small, and commonly approximately 8 to 10 mm in diameter and approximately 4 to 8 mm in height.

*Color.*—White, near White Group 155D.

*Fragrance.*—Slight and reminiscent of light musty dandelion fragrance.

*Duration.*—Flowering commonly lasts approximately two weeks and the duration is influenced by temperature.

*Fruit.*—None observed to date; however, no deliberate crossings have been attempted.

Hardiness: Performs well in U.S.D.A. Hardiness Zone Nos. 6(b) to 10.

Disease/pest resistance: Generally comparable to the *Photinia*×*fraseri* parent during observations to date. The variety during observations to date appears to be susceptible to the same diseases that afflict Photinia, such as *Entomosporium maculatum.*

I claim:

1. A new and distinct *Photinia*×*fraseri* plant having the following combination of characteristics:

(a) an upright outwardly-spreading broad-leaved evergreen shrub that has a more compact growth habit as the plant ages than commonly is displayed by *Photinia*×*fraseri,*

(b) forms distinctive variegated foliage that is initially reddish with pink margins, and with the margins finally maturing to near white with near white and silver splashes over the green median upper surfaces of the leaves, (c) propagates well by the use of stem cuttings, and (d) is well suited for providing attractive ornamentation in the landscape;

substantially as herein shown and described.

* * * * *

*Photinia* 'Cassini'